US006908614B2

United States Patent
Chung et al.

(10) Patent No.: US 6,908,614 B2
(45) Date of Patent: Jun. 21, 2005

(54) ANTI-AGING/MENOPAUSE SYMPTOMS RELIEF USING GANODERMA LUCIDUM SPORES

(76) Inventors: Chee-Keung Chung, Room 2018, Argyle Centre, 688 Nathan Road, Mongkok, Kowloon (HK); Siu Kan Tong, Room 2018, Argyle Centre, 688 Nathan Road, Mongkok, Kowloon (HK)

( * ) Notice: Subject to any disclaimer, the term of this patent is extended or adjusted under 35 U.S.C. 154(b) by 188 days.

(21) Appl. No.: 10/224,378

(22) Filed: Aug. 21, 2002

(65) Prior Publication Data

US 2003/0054014 A1 Mar. 20, 2003

Related U.S. Application Data

(60) Continuation-in-part of application No. 09/802,862, filed on Mar. 12, 2001, now Pat. No. 6,468,542, which is a division of application No. 09/524,508, filed on Mar. 13, 2000, now Pat. No. 6,316,002.
(60) Provisional application No. 60/158,377, filed on Oct. 12, 1999.

(51) Int. Cl.$^7$ ............................................. A61K 35/84
(52) U.S. Cl. ............................................. 424/195.15
(58) Field of Search ................................... 424/195.15

(56) References Cited

U.S. PATENT DOCUMENTS

| | | | |
|---|---|---|---|
| 4,472,907 A | 9/1984 | Wada et al. | |
| 5,667,999 A | 9/1997 | Koh et al. | |
| 6,316,002 B1 | 11/2001 | Liu et al. | |
| 6,399,116 B1 | 6/2002 | Xiu | |

FOREIGN PATENT DOCUMENTS

| | | | | |
|---|---|---|---|---|
| CN | 1105594 | * | 7/1995 | |
| CN | 1111529 | * | 11/1995 | |
| CN | 1119120 | * | 3/1996 | |
| CN | 1120953 | * | 4/1996 | |
| CN | 1130209 | * | 9/1996 | |
| CN | 1134306 A | | 10/1996 | .......... A61K/35/84 |
| CN | 1165032 A | | 11/1997 | .......... A61K/35/84 |
| CN | 1175464 | * | 3/1998 | |
| CN | 1122658 | * | 5/1998 | |
| CN | 1200296 | * | 12/1998 | |
| CN | 1223077 | * | 7/1999 | |
| CN | 1303622 A | | 7/2001 | |
| EP | 1 092 765 | | 4/2001 | |
| EP | 1 092 765 A | | 4/2001 | |
| JP | 2240026 | | 9/1990 | .......... A61K/35/84 |
| JP | 52041208 | | 8/1993 | .......... G03D/13/00 |
| JP | 2001207253 A | | 7/2001 | |
| JP | 2003063981 A | | 3/2003 | |
| WO | WO 0211744 A | | 2/2002 | |

OTHER PUBLICATIONS

Kindler, Christoph H. et al.; The Visual Analog Scale Allows Effective Measurement of Preopreative Anxiety and Detection of Patients' Anesthetic Concerns, Anesth Analog, vol. 90, p. 706–712 (2000).

Lee, Seung Y.; Cardiovascular Effects of Mycelium Extract of *Ganoderma lucidum*: Inhibition of Sympathetic Outflow as a Mechanism of Its Hypotensive Action, Chem Pharm. Bull. vol. 38, p. 1359–1364 (1990).
Kim et al., Int. J. Mol. Med vol. 4(3), p. 273–277 (1999).
Lin et al., J. Ethnopharmacol., vol. 47(1), p. 33–41 (1995).
Mekkawy, SaHar et al., Anti–HIV–1 and Anti–HIV–A–Protease Substances from *Ganoderma lucidum*; Phytochemistry, vol. 49(6), p. 1651–1657 (1998).
Wasser, Solomon P., et al., Therapeutic Effects of Substances Occuring in Higher Basidiomyceetes Mushrooms: A Modern Perspective; *Crit. Rev. Immunol.,* vol. 19(1), p. 65–96 (1999).
Miyazaki, Toshio et al., Studies on Fungal PolysaccharidesXXVIL Structural Examination of a Water–soluble, Antitumor Polysaccharide of *Ganoderma lucidum*; *Chem. Pharm. Bull.,* vol. 29(12), p. 3611–3616 (1981).
Min, Byung–Sun et al.; Triterpenes from the Spores of *Ganoderma lucidum* and Their Inhibitory Activity against HIV–1 Protease; *Chem. Pharm. Bull.,* vol. 46(10), p. 1607–1612 (1998).
Kino, K. et al.; An immunomodulating protein, Ling Zhi–8(LZ–8) prevents insulitis an non–obese diabetic mice; *Diabetologia,* vol. 33 p. 713–718 (1990).
Lieuwe, G. et al.; Ling Zhi–8: Studies of a New Immuno–modulating Agent; *Transplantation,* vol. 60, p. 438–443 (1995).
Kino, Kohsuke et al.; Immunomodulator, LZ–8, Prevents Antibody Production in Mice; *Int. J. Immunopharmac.,* vol. 13(8), p. 1109–1115 (1991).
Maruyama, Hirotumi; Antitumor Activity of *Sarcodon aspratus* (BERK>) S. Ito and *Ganoderma lucidum* (FR.) Karst.; *J. Pharmacobio–Dyn.,* vol. 12, p. 118–123 (1989).
Shimizu, Akira et al.; Isolation of an Inhibitor of Platelet Aggregation from a Fungus, *Ganoderma lucidum*; *Chem. Pharm. Bull.,* vol. 33, p. 3012–3015 (1985).
Morigiwa, Aiko et al.; Angiotension Converting Enzyme–Inhibitory Triterpenes from *Ganoderma lucidum*; *Chem. Pharm. Bull.,* vol. 34(7), p. 3025–3028 (1986).
Kanmatsuse, Katsuo et al.; Studies on *Ganoderma lucidum.* I. Efficacy against Hypertension and Side Effects; *Yakugaku Zasshi,* vol. 105(10), p. 942–947 (1985).

(Continued)

*Primary Examiner*—Christopher R. Tate
(74) *Attorney, Agent, or Firm*—Fei-Fei Chao; Bingham McCutchen LLP

(57) ABSTRACT

The present invention provides a method for preventing/slowing aging and/or reducing menopause symptoms in humans by orally administering an effective amount of germination-activated *Ganoderma lucidum* spores (GLSs) to humans. The treatment for menopause is especially effective in male patients. GLSs are effective as an antioxidant to reduce free radical damage, particularly by increasing the amount of the reduced form glutathione (GSH) and the superoxide dismutase (SOD) activity. GLSs can also increase testosterone level in blood and improve depression, particularly geriatric depression, in elderly male patients.

12 Claims, No Drawings

OTHER PUBLICATIONS

Lieu, Chien–Whei et al.; The Effect of *Ganoderma lucidum* on Induction of Differentiation in Leukemic U937 Cells; *Anticancer Research,* vol. 12, p. 1211–1216 (1992).

Wang, Sheng–Yuan et al.; The Anti–Tumor Effect of *Ganoderma lucidum* is Mediated by Cytokines Released from Activated Macrophages and T Lymphocytes; *Int. J. Cancer,* vol. 70, p. 699–705 (1997).

O'Neil, Carol E. et al.; Basidiospore Extracts: Evidence for Common Antigenic/Allergenic Determinants; *Int. Archs Allergy appl. Immun.,* vol. 85, p. 161–166 (1988).

Nogami, Mari et al.; Studies on *Ganoderma lucidum*VI. Anti–allergic Effect. (1); *Yakugaku Zasshi,* vol. 106(7), p. 594–599 (1986).

Liu, Gengtao et al.; Some Pharmacological Actions of the Spores of *Ganoderma lucidum* and the Mycelium of *Ganoderma capense* (Lloyd)Teng Cultivated by Submerged Fermentation; *Chinese Medical Journal,* vol. 92(7), p. 496–500 (1979).

Fu, Huidi et al.; The Clinical Effects of *Ganoderma lucidum* Spore Preparations in 10 Cases of Atrophic Myotonia; *Journal of traditional Chinese Medicine,* vol. 2(!), p. 63–65 (1982).

Mizushina, Yoshiyuki et al.; A Mushroom Fruiting Body–Inducing Substance Inhibits Activities of Replicative DNA Polymerases; *Biochemical and Biophysical Research Communications,* vol. 249, p. 17–22 (1998).

Lin, Lee–Juian et al.; Separation of oxygenated triterpenoids from *Ganoderma lucidum* by high–performance liquid chromatography; *Journal of Chromatography,* vol. 410, p. 195–200 (1987).

Kino, Kohsuke et al.; Isolation and Characterization of a New Immunomodulatory Protein, Ling Zhi–8 (LZ–8), from *Ganoderma lucidum; The Journal of Biological Chemistry,* vol. 264, p. 472–478 (1989).

FDA: "*Ganoderma Lucidum* Spore Powder", 'Online! Aug. 18, 1999, pp. 1–35, XP–002257875.

Database EPODOC 'Online!, European Patent Office, The Hague, NL; XP002257877 (Abstract Only).

Database EPODOC 'Online!, European Patent Office, The Hague, NL; XP002257878(Abstract Only).

Byung–Sun Min et al., "Triterpenes from the Spores of *Ganoderma lucidum* and Their Inhibitory Acitivy against HIV–I Protease", Chemical and Pharmaceutical Bulletin, Pharmaceutical Society of Japan, vol. 46, No. 10, Oct. 1998, p. 1607–1612.

Avraham Margalit et al., "Reducing the expected computational cost of template matching using run length representation", Pattern Recognition Letters, No. 4, Apr. 11, 1990, pp. 255–255–265.

Y. W. Ho et al., "Germination Studies of *Ganoderma–Boninense* Spores From Oil Palms In Malaysia", Pertanika, vol. 9, No. 2, 1986, pp. 151–154.

Y. W. Ho et al., "Spore production of *Ganoderma boninense* Pat. And the effect of pH, light and dryness on germination", Journal of Plant Protection in the Tropics10(1), pp. 51–58.

W–L Lu et al., "Studies of some biological characteristics of sporophore of *ganoderma–Lucidum* in Culture" Acta Bontanica Sinica, vol. 17, No. 2, 1975, pp. 153–160, XP009019108 (Chinese Language).

Database EPODOC 'Online!, European Patent Office, The Hague, NL; XP002257879 (Abstract Only).

Solomon P. Wasser[1,3] et al., "Therapeutic Effects of Substances Occuring in Higher Basidiomycetes Mushrooms: A Modern Perspective" Critical Reviews in Immunology, 1999, pp. 65–96, vol. 19, No. 1.

Database EPODOC 'Online!, European Patent Office, The Hague, NL; XP002257880 (Abstract Only).

\* cited by examiner

ANTI-AGING/MENOPAUSE SYMPTOMS RELIEF USING GANODERMA LUCIDUM SPORES

CROSS-REFERENCE TO RELATED APPLICATIONS

The present application is a continuation-in-part (CIP) of U.S. patent application Ser. No. 09/802,862, filed on Mar. 12, 2001 now U.S. Pat. No. 6,468,542, which is a divisional application of U.S. patent application Ser. No. 09/524,508, filed on Mar. 13, 2000 and issued as U.S. Pat. No. 6,316,002, which in turn claims the priority of U.S. provisional application No. 60/158,377, filed on Oct. 12, 1999, wherein all of the U.S. priority applications are herein incorporated by reference.

FIELD OF THE INVENTION

The present invention relates to a method for preventing/slowing an aging process and/or reducing/relieving menopause symptoms in humans by orally administering an effective amount of germination-activated *Ganoderma lucidum* spores ("GLSs") to humans. The anti-aging effect of GLSs is primarily derived from its being an antioxidant for free radical protection. GLSs also reduce and/or relieve symptoms associated with menopause, particularly male menopause, which are partially due to aging. Symptoms associated with male menopause include fatigue, anorexia, palpitation, forgetfulness, irritation, depression, and/or impotence.

BACKGROUND OF THE INVENTION

The free radical theory of aging was first proposed by Dr. Denham Harman in 1956. It is now recognized that living cells continuously produce free radicals during their normal functions such as producing energy. Free radicals also come from smoking, radiation, sunlight and other factors in the environment. Endogenous and exogenous free radicals are highly reactive substances, capable of reacting irreversibly with many biological molecules, producing random changes, and causing progressive deterioration of the biological system.

The cells have an antioxidant defense system which prevents most, but not all, of the free radical damages. Constant free radical damages can eventually kill the cells. When free radicals kill or damage enough cells in an organism, the organism ages.

The antioxidant defense system removes free radicals through the use of antioxidants. There is sufficient evidence to support the relationship between free radicals and aging. For example, the longer an animal lives, the more antioxidants it has in its body. Some antioxidants are produced by the body through endogenous enzymes, such as catalase, glutathione peroxidases (GPX) and superoxide dismutases (SOD). Others come from oral ingestion, such as vitamin C, vitamin E, β-carotene, selenium etc. It is believed that taking antioxidants to remove access free radicals in the body can slow down the aging process. Some studies show that antioxidants may help prevent heart disease, some cancers, cataracts, and other health problems that are more common as people get older.

One of the aging problems men face is the occurrence of male menopause. It has been estimated approximately 40% of men in their 40s, 50s, and 60s will experience some degree of male menopause. Also known as andropause, male menopause is of recent recognition with researches first published in 1970s.

Less overwhelming than the female menopause, male menopause is more gradual and some never experience it. Male menopause involves the hormonal, physiological and chemical changes that occur in men generally between the ages of 40 and 55. It is characterized with lethargy, depression, increased irritability, mood swings, decreased libido, erectile dysfunction and alteration in cognition. Although its causes have not been fully researched, factors such as hormone deficiencies, excessive alcohol consumption, smoking, hypertension, medications, poor diet, lack of exercise, poor circulation and psychological problems have been known to contribute to this condition.

It has been found the blood level of the male hormone testosterone decreases significantly even in healthy men by age 55, when comparing to what it is at age 45. In fact, by age 80, most male hormone levels have decreased to pre-puberty levels. Low testosterone has been associated with fatigue, depression, loss of concentration, and decreased muscle strength and endurance.

Depression is another common denominator of male menopause. According to the Epidemiologic Catchment Area Study in the 1991 NIH Consens Statement, depressive symptoms occur in approximately 15 percent of community residents over 65 years of age. Patients may suffer from depressed mood, loss of appetite, sleeplessness, anergia and loss of interest and enjoyment of the normal pursuits of life. Depression is often underdiagnosed and undertreated in the elderly, partially because the health care providers and/or the patients themselves often conclude that depression is a normal consequence of physical illnesses, as well as social and economic problems associated with the elderly. At this time, there is no one best agent that provides comprehensive relief for symptoms associated with male menopause, particularly for the elderly.

*Ganoderma* (*Ganoderma lucidum* Leyss ex Fr. Karst) is a polyporous fungus. It belongs to the class Basidiomycetes, the family Polypolaceae, and the genus *Ganoderma*. Since ancient times, *ganoderma* has been praised as a miracle fungus for its capability of prolonging human life. It is believed that the medicinal effects of *ganoderma* lie upon the natural or bioactive substances it produces which can stimulate or modulate the neuro-endocrino-immuno system of human body to fight off diseases. *Ganoderma* is also well known for its antitumor and immune enhancing properties, (Kim et al., Int. J. Mol. Med. (1999), 4(3):273–277), cardiovascular effects (Lee et al., Chem. Pharm. Bull. (1990), 38:1359–1364), as well as free radical scavenging and antihepatotoxic activities (Lin et al., J. Ethnopharmacol., (1995), 47(1):33–41).

*Ganoderma* is the most rare and valuable herb in Chinese medicine. It is known in China for over 5,000 years as "ling zhi". There are a variety of *ganoderma*, for instance, *G. lucidum* (red), *G. applanatum* (brown), *G. tsugae* (red), *G. sinense* (black), and *G. oregonense* (dark brown). However, due to the fact that wild types of *ganoderma* only grow naturally and very rarely on aged trees in steep mountains, research which requires a constant supply of high quantity and quality of *ganoderma* has rarely been conducted.

Although it is believed that the spores of *ganoderma* represent the essence of *ganoderma* because they contain all the bioactive substances of *ganoderma*, most of the *ganoderma* studies are conducted using the fruit body or mycelium of *ganoderma* as experimental materials. *Ganoderma* spores are rarely studied.

*Ganoderma* spores are tiny and mist-like spores of 5~8 μm in sizes which have extremely hard and resilient, double-layer epispores, thus making them difficult to break open. The *ganoderma* spores normally scatter at the pelius of mature *ganoderma*. When mature, the *ganoderma* spores are ejected from the pileus. Such ejected *ganoderma* spores are collectively called "spore powders". In the wild, the "spore powders" are difficult to collect because of the following reasons: (1) the germination rate (i.e., about 3–15%) of the spores is extremely low; (2) the ejection period is relatively short (i.e., approximately 10 days per lifecycle); and (3) some environmental factors, such as wind and rain, may also hinder the collection of the spores. In addition, the substances of the collected spores are difficult to extract due to the resiliency of the epispores.

In recent years, with the improvement of the spore breaking techniques, more research which directed to the studies of the *ganoderma* spores has been undertaken. However, the improvement of the spore breaking techniques does not overcome the shortcoming of the low germination rate of the spores. In fact, due to the low germination rate, most of the studies on *ganoderma* spores are conducted using the extraction of bioactive substances from spores representing an array of dormant to various germination stages. Because the spores at different stages of the lifecycle produce different kinds and/or proportions of bioactive substances, each batch of the mixture of the spores thus contains different active ingredients. The results from such studies are apparently meaningless since no proper controls can be provided.

A germination activation method is disclosed in the parent application of the present application, which was issued as U.S. Pat. No. 6,316,002 B1, which is herein incorporated by reference. The method provides successfully activation of the dormant *ganoderma* spores and increase the germination rate of the *ganoderma* spores to more than 95%.

In the invention to be presented below, a method for using the germination activated *Ganoderma lucidum* spores ("GLSs") as free radical scavenger (i.e., antioxidant) and anti-aging agent, particularly for reducing/relieving symptoms associated with male menopause, will be introduced. GLSs possess multiple biological activities and promotes general health. Particularly, its activities in removal of free radicals, promotion of hormonal production and antidepression render GLSs effective for treating conditions associated with old ages (i.e., anti-aging) and male menopause.

SUMMARY OF THE INVENTION

The present invention provides a method for preventing/slowing the aging process and/or reducing/relieving menopause-associated symptoms in humans. The method requires oral uptake of germination activated *Ganoderma lucidum* spores (GLSs).

One of the factors that affect the aging process is free radical damage. GLS is an antioxidant. GLSs, when orally given to humans in the amount of about 0.5 to 10 g per day, preferably about 1 to 5 g per day, demonstrate antioxidant effect which protects the body from free radical damage. For example, GLSs increase the amount of the reduced form of glutathione (GSH) and the activity of superoxide dismutase (SOD) in the human body.

Symptoms related to male menopause are fatigue, anorexia, palpitation, forgetfulness, irritation, depression, impotence, and any combination thereof. Male menopause is particularly significant in elderly male.

To reduce or relieve the symptoms of male menopause, about 0.5 to 10 g of GLSs, more favorably about 1 to 5 g of. GLSs, are given to the patient per day. GLSs increase the blood level of testosterone and superoxide dismutase (SOD) activity in patients. GLSs also decrease the blood level malondialdehyde (MDA) in patients. In addition, GLSs improve depression of patient, particularly the elderly.

DETAILED DESCRIPTION OF THE INVENTION

The tiny spore of *Ganoderma lucidum* has an extremely hard and resilient, double-layered epispore. In the wild, the germination of the spores of *Ganoderma lucidum* is relatively slow and their germination rate is extremely low. In fact, it takes about 24 to 48 hours for the germ tubes of the spores start to sprout under proper conditions, and the capillitia start to form branches after 72 hours, with a germination rate of only 3–15%.

Mature spores of *Ganoderma lucidum* were selected to undergo processing treatment. There are three distinctive stages for the spores processing treatment so as to effectively preserve the large amount of bioactive substances produced by the germination activated spores. The first stage involves the induction of germination, which is achieved by soaking the spores in a solution for a period of time, followed by cultivating the germination induced spores in a well-ventilated culture box. The second stage involves the production of sporoderm-broken (i.e., by breaking up the cell walls of epispores) spores, which is achieved by enzyme treatment and/or mechanical force. The final stage involves the extraction of bioactive substances from the sporoderm-broken spores, which is achieved by freeze-drying or vacuum drying followed by extraction with solvent or by thin film condensation.

Below are general descriptions of the steps which lead to the production of bioactive substances:

I. Soaking to induce germination: Mature and perfect spores of *Ganoderma lucidum* were carefully selected to undergo a soaking process to induce germination. Spores were kept in clear or distilled water, biological saline solution, or other nutritional solutions that could enable the spores of red *Ganoderma lucidum* to germinate rapidly. Examples of nutritional solutions include coconut juice or a 1–5% malt extract solution, 0.5–25% extracts of *Ganoderma lucidum* sporocarps or *Ganoderma lucidum* capillitia, 0.1–5% of culture solution containing biotin, 0.1–3% of culture solution containing potassium phosphate (monobasic) and magnesium sulfate. The choice of solution would depend on the soaking time required, the amount of spores to be processed and other such factors as availability of materials. One or more of the above germination solutions could be used, with the amount added being 0.1–5 times the weight of the spores of red *Ganoderma lucidum*. The soaking time was determined according to the temperature of the water, and usually the soaking was carried out for 30 min to 8 hours with the temperature of the water at 20–43° C. Preferably soaking times were 2–4 hours, and temperature of the water was 25–35° C.

II. Activation culture: The spores of *Ganoderma lucidum* were removed from the soaking solution and excess solution was eliminated by allowing it to drip. The spores were then placed in a well-ventilated culturing box at a constant temperature and humidity so that spore activation culture could be carried out. The relative humidity of the culture was generally set at 65–98%, the culture temperature at 18–48° C. and the activation time lasted from 30 min to 24 hours. Preferably humidity is 85–97% and temperature is 25–35° C. Using this method, the activation of spores of red *Ganoderma lucidum* reached a rate of more than 95%. During activation, the cell walls of the spores of red *Gano-*

*derma lucidum* were clearly softened such that it was easier to penetrate the cell walls of the spores.

III. Treatment of the epispores: After the germination activation process, the spores were treated by enzymolysis. This process was carried out at a low temperature and under conditions such that enzyme activity was maintained, using chitinase, cellulase, or other enzymes, which are commonly used in the industry. The process was complete when the epispores lost their resilience and became brittle. Alternatively, physical treatments were carried out to penetrate the cell walls, for example, micronization, roll pressing, grinding, super high pressure microstream treatment, and other mechanical methods commonly used in the industry could be carried out, with a penetration rate of over 99%.

IV. Drying/Encapsulation: Drying was carried out at low temperature using standard methods including freeze-drying or vacuum-drying etc., which are commonly used in the industry. The obtained product had a moisture content less than 4%. The dried GLSs are in powder form and encapsulated. Each capsule contains 300 mg of dried GLSs.

The preferable dosage for oral GLSs uptake is about 2–4 capsules per time, 1–3 times per day.

In describing the invention, specific terminologies are employed. For the sake of clarity, these terminologies are explained as follows. It is to be understood that each specific term includes all technical equivalents which operate in a similar manner to accomplish a similar purpose.

The term "free radicals" refers to a group of highly active substances that are constantly produced in the process of cellular metabolism and can have damaging effect on organisms. Free radicals are atoms with unpaired electrons. Mitochondria, regions of the cell that manufacture chemical energy, produce free radicals and are the primary sites for free radical damage. Free radicals can induce oxidation reactions, cause proteins to crosslink and be damaged, decrease the activity of enzymes, contribute to an abnormal metabolism of the nucleic acid, and cause superoxidation of the polyunsaturated lipids in the biological membranes. The results of free radical attack can lead to damage to the cellular structures and functions as well as the various organs in an organism, thus resulting in aging and multiple pathologies.

The term "glutathione" or "GSH" is referred to the reduced form of glutathione. Glutathione is a low molecular-weight scavenger of the body. The ubiquitous tripeptide L-glutathione (GSH) (gamma-glutamyl-cysteinyl-glycine) is a well-known biological antioxidant, and in fact is believed to be the primary intracellular antioxidant for higher organisms. When oxidized, it forms a dimer (GSSG), which may be recycled in organs having glutathione reductase. GSH is one of the primary cellular antioxidants responsible for maintaining the proper oxidation state within the body. GSH is synthesized by most cells, and is also supplied in the diet. GSH has been shown to recycle oxidized biomolecules back to their active, reduced forms. GSH is, in the human adult, produced from oxidized glutathione (GSSG) primarily by the liver, and to a smaller extent, by the skeletal muscle, red blood cells, and white cells. A deficiency of glutathione in cells may lead to excess free radicals, which cause macromolecular breakdown, lipid peroxidation, buildup of toxins, and ultimately cell death. Because of the importance of glutathione in preventing this cellular oxidation, glutathione is continuously supplied to the tissues. The level of GSH in the tissues is an important factor in evaluating the anti-oxidative capability of the body.

The term "superoxide dismutase" or "SOD" refers to a metalloenzyme which catalyze the dismutation of superoxide ion into oxygen and hydrogen peroxide. There are three classes of SODs, each characterized by the catalytic metal at the active site, namely, Cu/Zn-SOD, Mn-SOD and Fe-SOD. Cu/Zn-SOD is found primarily in eukaryotes. Fe-SOD is found mainly in prokaryotes. Mn-SOD crosses the entire range from prokaryotes to eukaryotes. In human, the Cu/Zn-SOD is localized in the cytosol and nucleus, while Mn-SOD is located in the mitochondrial matrix. SOD has a high molecular weight and cannot be absorbed into the human body by oral administration.

The term "malondialdehyde" or "MDA" refers to the toxic and mutagenic compound malondialdehye. MDA is a product of the secondary reduction of lipid peroxidation, that is, a metabolite of lipid peroxidation. It is a compound with two functional groups and can react with compounds that contain amino groups, such as proteins, nucleic acids, cephalins, etc., causing them to cross-link and thus lose their functions, with the result of protein denaturation, loss of enzyme activity, and damage to the DNA. Animal tests show that MDA is also a strong carcinogen which can induce tumors in animals. Measurement of MDA in tumor tissues can directly reflect the extent of lipid peroxidation caused by the tumors.

The term "male menopause" refers to the hormonal, physiological and chemical changes that occur in all men generally between the ages of 40 and 55.

The term "SRS" refers to Supervison Rating Scale. SRS measures the level of supervision that a patient/subject receives from caregivers. The SRS rates level of supervision on a 13-point ordinal scale that can optionally be grouped into five ranked categories (Independent, Overnight Supervision, Part-Time Supervision, Full-Time Indirect Supervision, and Full-Time Direct Supervision). The SRS was designed to be rated by a clinician based on interviews with the subject and an informant who has observed at first hand the level of supervision received by the subject.

The term "Zung Self-Rating Depression Scale" or "Self-Rating Depression Scale of Zung" refers to an instrument for assessing depression simply and specifically using traits found in the depressive disorders. It is named after Zung W W, Arch. Gen. Psychiat. (1965) 12:63–70.

The following examples are illustrative, but not limiting the scope of the present invention. Reasonable variations, such as those occur to reasonable artisan, can be made herein without departing from the scope of the present invention. Also, in describing the invention, specific terminology is employed for the sake of clarity. However, the invention is not intended to be limited to the specific terminology so selected. It is to be understood that each specific element includes all technical equivalents which operate in a similar manner to accomplish a similar purpose.

EXAMPLE 1

Effects of GLSs on Mice Hepatic Glutathione (GSH) Contents

Glutathione (GSH) is a low molecular-weight scavenger of the body. It can remove $O_2.^-$ or $H_2O_2$. The contents of GSH in the tissues are an important factor in evaluating the anti-oxidative capability of the body.

1. Materials and Methods 1.1 Materials

Sixty (60) NIH mice, half males and half females, weighing 18–22 g were obtained from Guangdong Provincial Animal Center for Medical Experiments, Certificate of Conformity Number: 26-2001A008 (for animal inspection) and 26-2001B008 (for animal facility).

Germination activated *Ganoderma lucidum* spores ("GLSs") (0.2 g/mL) were obtained from Guangzhou Green Food Project Company of the College of Life Sciences, Zhongshan University and Green Power Health Products International Co. Ltd., Sweden and Hong Kong.

1.2 Instruments and Test Reagents

Test instruments included: 752 UV-Vis spectrometer; TL-16 high speed tabletop refrigerated centrifuge; CS-502 super constant-temperature water bath; SL122 electronic balance; and vortex.

Test reagents included: GSH test kit, provided by Jenchun Biotech Research Institute, Nangjing, China; and total protein test kit, provided by Chungshen Biotech Hi-tech Co., Beijing, China.

1.3 Methods

The mice were randomized into 5 groups of 12 mice. The four treatment groups received 1 g/kg/day, 2 g/kg/day, 4 g/kg/day, or 8 g/kg/day of GLSs via gavage for 15 consecutive days. The control group received daily saline via gavage for 15 consecutive days.

On the day after the treatment period, the animals were sacrificed and the livers were removed. A 10% homogenate was prepared from each accurately weighed liver tissue of about 0.2 g and centrifuged. A 30 μL aliquot of each supernatant was removed and tested for GSH and protein contents, using the GSH test kit and the total protein test kit. The GSH content was then expressed as mg/mg protein.

2. Results

As shown in Table 1, when comparing with the control group, all treatment groups exhibited statistically significant increases (paired t test, $p<0.01$) of the GSH contents in the hepatic tissues.

TABLE 1

Effects of GLSs on Mice Hepatic GSH Contents ($\bar{x} \pm s$)

| Group | Dose (g/kg/day) | Animal number (before/after treatment) | Glutathione ($\bar{x} \pm s$) (mg/mg protein) | p value (vs control) |
|---|---|---|---|---|
| Control | 20 mL saline | 12/12 | 41.5 ± 5.4 | — |
| Treatment | 1 | 12/12 | 51.5 ± 5.1 | <0.01 |
| Treatment | 2 | 12/12 | 56.5 ± 6.2 | <0.01 |
| Treatment | 4 | 12/12 | 59.5 ± 5.8 | <0.01 |
| Treatment | 8 | 12/12 | 64.5 ± 0.41 | <0.01 |

3. Conclusion

The results of this experiment demonstrate that GLSs significantly increased the GSH contents in the NIH mice. This suggested that under the present experiment conditions, GLSs possessed anti-aging and antioxidant activity, as evidenced by its ability to increase the GSH contents in the body.

EXAMPLE 2

Effects of GLSs on Mice Hepatic Superoxide Dismutase (SOD) Activity

1. Materials and Methods 1.1 Materials

Sixty (60) NIH mice, half males and half females, weighing 18–22 g were obtained from Guangdong Provincial Animal Center for Medical Experiments, Certificate of Conformity Number: 26-2001A009 (for animal inspection) and 26-2001B008 (for animal facility).

Germination activated *Ganoderma lucidum* spores (GLSs) in powder form was obtained from Guangzhou Green Food Project Company of the College of Life Sciences, Zhongshan University and Green Power Health Products International Co. Ltd., Sweden and Hong Kong. The GLSs was dissolved in a suitable aqueous solution to a final concentration of 0.2 g/mL.

1.2 Instruments and Test Reagents

Test instruments included: 752 UV-Vis spectrometer; TL-16 high speed tabletop refrigerated centrifuge; CS-502 super constant-temperature water bath; SL122 electronic balance; and vortex.

Test reagent included: SOD test kit, provided by Jenchun Biotech Research Institute, Nangjing, China. The enzyme activity of SOD was calculated as nmol/mL.

1.3 Method

Sixty (60) mice were randomly separated into 5 groups (4 treatment groups and 1 control group), each having 12 mice. The four treatment groups received 1 g/kg/day, 2 g/kg/day, 4 g/kg/day, or 8 g/kg/day of GLSs via gavage for 15 consecutive days. The control group received daily saline via gavage for 15 consecutive days.

On the day after the completion of the treatment period, the animals were sacrificed and the livers were removed. Approximately 0.2 g of liver tissue from each animal was taken and added to 2 mL of saline solution to form a 10% homogenate by homogenization. The homogenate was centrifuged. A 30 μL aliquot of the supernatant from each homogenate was taken and tested for SOD using the SOD test kit.

2. Results

As shown in Table 2, when comparing with the control group, all treatment groups exhibited statistically significant increases (paired t test, $p<0.01$–$0.05$) in the total hepatic SOD (T-SOD) enzyme activities in mice.

TABLE 2

Effects of GLSs on Mice Hepatic T-SOD Enzyme Activities ($\bar{x} \pm s$)

| Group | Dose (g/kg/day) | Animal number (before/after treatment) | T-SOD ($\bar{x} \pm s$) (nmol/mL) | p value (vs control) |
|---|---|---|---|---|
| Control | 20 mL saline | 12/12 | 152.1 ± 10.8 | — |
| Low dose | 1 | 12/12 | 172.5 ± 9.1 | <0.05 |
| Medium low dose | 2 | 12/12 | 189.2 ± 8.0 | <0.01 |
| Medium high dose | 4 | 12/12 | 192.4 ± 10.2 | <0.01 |
| High dose | 8 | 12/12 | 205.4 ± 11.0 | <0.01 |

T-SOD: total SOD

As shown in Table 3, when comparing with the control group, all treatment groups exhibited statistically significant increases (paired t test, $p<0.01$–$0.05$) in hepatic Cu.Zn-SOD enzyme activities.

TABLE 3

Effects of GLSs on Mice Hepatic Cu.Zn-SOD Enzyme Activities ($\bar{x} \pm s$)

| Group | Dose (g/kg/day) | Animal number (before/after treatment) | Cu.Zn-SOD ($\bar{x} \pm s$) (nmol/mL) | p value (vs control) |
|---|---|---|---|---|
| Control | 20 mL saline | 12/12 | 70.3 ± 10.1 | — |
| Low dose | 1 | 12/12 | 85.2 ± 9.8 | <0.05 |

TABLE 3-continued

Effects of GLSs on Mice Hepatic Cu.Zn-SOD Enzyme Activities ($\bar{x} \pm s$)

| Group | Dose (g/kg/day) | Animal number (before/after treatment) | Cu.Zn-SOD ($\bar{x} \pm s$) (nmol/mL) | p value (vs control) |
|---|---|---|---|---|
| Medium low dose | 2 | 12/12 | 92.1 ± 9.6 | <0.01 |
| Medium high dose | 4 | 12/12 | 99.2 ± 9.0 | <0.01 |
| High dose | 8 | 12/12 | 109.1 ± 9.8 | <0.01 |

As shown in Table 4, when comparing with the control group, all treatment groups exhibited statistically significant increases (paired t test, p<0.01–0.05) in the hepatic Mn-SOD enzyme activities.

TABLE 4

Effects of GLSs on Mice Hepatic Mn-SOD Enzyme Activities ($\bar{x} \pm s$)

| Group | Dose (g/kg/day) | Animal number (before/after treatment) | Mn-SOD ($\bar{x} \pm s$) (nmol/mL) | p value (vs control) |
|---|---|---|---|---|
| Control | 20 mL saline | 12/12 | 80.8 ± 9.0 | — |
| Low dose | 1 | 12/12 | 85.9 ± 10.1 | <0.05 |
| Medium low dose | 2 | 12/12 | 88.6 ± 9.8 | <0.01 |
| Medium high dose | 4 | 12/12 | 93.1 ± 10.0 | <0.01 |
| High dose | 8 | 12/12 | 96.1 ± 9.8 | <0.01 |

3. Conclusion

The results showed that treatment with GLSs for 15 days markedly increased the hepatic SOD enzyme activities in the NIH mice. When comparing with the control group, total SOD (T-SOD), cytosolic SOD (Cu.Zn-SOD), and mitochondrial SOD (Mn-SOD) enzyme activities all showed statistically significant increases at all dose levels. This suggested that under the present experiment conditions, GLSs possessed anti-oxidant activity.

EXAMPLE 3

Effects of GLSs on Mice Hepatic Malondialdehyde (MDA) Contents

Oxygen free radicals produced by enzymatic or non-enzymatic reactions in the body attack the polyunsaturated fatty acids (PUFA) in the biological membranes. These attacks can result in peroxidation of the lipids; formation of lipid peroxides, containing functional groups such as aldehyde (eg., malondialdehyde, MDA), ketone, hydroxyl, carbonyl, hydrogen peroxide, peroxides, etc.; and formation of new free radicals, etc. Thus, the level of MDA reflects the degree of lipid peroxidation and indirectly correlated to the severity of cell damage.

The MDA measurement is often combined with the SOD findings for evaluation of the cellular functions. The SOD activity indicates the cellular ability to remove oxygen free radicals and the MDA level reflects the severity of cell damages due to oxygen free radical attacks.

1. Materials and Methods 1.1 Materials

Sixty (60) NIH mice, half males and half females, weighing 18–22 g were obtained from Guangdong Provincial Animal Center for Medical Experiments, Certificate of Conformity Number: 26-2001A008 (for animal inspection) and 26-2001B008 (for animal facility).

Germination activated *Ganoderma lucidum* spore powder was obtained from Guangzhou Green Food Project Company of the College of Life Sciences, Zhongshan University and Green Power Health Products International Co. Ltd., Sweden and Hong Kong. The GLSs was dissolved in a suitable aqueous solution to a final concentration of 0.2 g/mL.

1.2 Instruments and Test Reagents

Test instruments included: 752 UV-Vis spectrometer; TL-16 high speed tabletop refrigerated centrifuge; CS-502 super constant-temperature water bath; SL122 electronic balance; and vortex.

Test reagent included MDA test kit, provided by Jenchun Biotech Research Institute, Nangjing, China.

1.3 Method

Sixty (60) mice were randomly separated into 5 groups (4 treatment groups and 1 control group), each with 12 mice. The four treatment groups received 1 g/kg/day, 2 g/kg/day, 4 g/kg/day, or 8 g/kg/day of GLSs, respectively, via gavage for 15 consecutive days. The control group received saline daily via gavage for 15 consecutive days.

On the day after the completion of the treatment period, the animals were sacrificed and the livers were removed. A 10% homogenate was prepared by homogenizing about 0.2 g of liver tissue in about 2 mL of homogenization solution. The homogenate was centrifuged. A 10 $\mu$L aliquot of supernatant from each homogenate was removed and tested for MDA using the MDA test kit.

2. Results

As shown in Table 5, when comparing with the control group, all treatment groups exhibited statistically significant less MDA (paired t test, p<0.01) in the hepatic tissues.

TABLE 5

Effects of GLSs on Mice Hepatic MDA Contents ($\bar{x} \pm s$)

| Group | Dose (g/kg/day) | Animal number (before/after treatment) | MDA ($\bar{x} \pm s$) (nmol/mL) | p value (vs control) |
|---|---|---|---|---|
| Control | 20 mL saline | 12/12 | 7.95 ± 0.95 | — |
| Treatment | 1 | 12/12 | 6.6 ± 0.81 | <0.01 |
| Treatment | 2 | 12/12 | 5.02 ± 0.71 | <0.01 |
| Treatment | 4 | 12/12 | 4.01 ± 0.82 | <0.01 |
| Treatment | 8 | 12/12 | 3.02 ± 0.51 | <0.01 |

3. Conclusion

The results of this experiment showed that GLSs effectively reduced the MDA contents in the NIH mice. This suggested that under the present experiment conditions, GLSs possessed anti-oxidant activity in preventing or reducing the MDA synthesis in the body.

EXAMPLE 4

Effects of GLSs on Treating Male Menopausal Symptoms in Humans

Menopausal Symptoms in men, particularly elderly men, have been a health concern. More and more evidence indicates that, in addition to the decreases in production and function of male sex hormone, the overall level of total body metabolism (e.g., microcirculation metabolism, blood viscosity, metabolism of oxygen free radicals, etc.) can affect the physical and mental status of the elderly men. It has been hypothesized that improving the total body metabolism may assist in delaying the onset of dementia, improving the cognitive functions, alleviating depression, elevating testosterone level, and regulating neurotransmitter and brain receptor functions.

1. Materials and Method 1.1 Test Materials

Germination activated *Ganoderma lucidum* spores (GLSs) in capsules were obtained from Guangzhou Green Food Project Company of the College of Life Sciences, Zhongshan University and Green Power Health Products International Co. Ltd., Sweden and Hong Kong. Each capsule contained about 300 mg of GLSs.

1.2 Inclusion Criteria

Male patients fulfilled the following criteria were admitted to the trial:

(1) ages 55–76 years old;

(2) having menopausal symptoms (e.g., fatigue, insomnia, blood vessel constriction, mental & psychological symptoms, sexual dysfunction) for 6 months–2 years;

(3) blood testosterone level lower than the normal value (140 ng/dL);

(4) no severe cerebral cardiovascular diseases, no contagious diseases and no diagnosis of tumors;

(5) score higher than 16 in the SRS self-evaluation for middle-age and elderly men; and (6) score higher than or equal to 50 in Zung's depression quantification scores.

1.3 Study Site

The study was conducted at the Urology Surgical Department of Guangzhou First People's Hospital, Guangdon Province, China.

1.4 Study Procedure

Before treatment initiation, baseline medical history, Zung's score (Zung Self-Rating Depression Scale), and SRS scores were collected from patients. Arterial blood sample from each patient was collected in the morning on empty stomach and measured for testosterone, red blood cell SOD and MDA levels in the blood.

The treatment group received GLSs 2 capsules (approximately 600 mg of GLSs) three times a day for 3 weeks with no concomitant treatment for any mental/psychological diseases. The control group received placebo. All patients were evaluated once a week for symptoms, SRS score and Zung's score. Arterial blood sample of each patient was collected at the end of the 3-week treatment and measured for testosterone, red blood cell SOD and MDA levels in the blood.

2. Results

A total of 138 eligible males, average age of 66 years old, were enrolled in the study. Average duration of menopausal symptoms was 12.3 months. Of the 138 patients, were single. Eighty (80) patients were assigned to the treatment group and 58 were in the control group.

As shown in Table 6, after 3 weeks of treatment, patients in the treatment group demonstrated statistically significant improvements ($p<0.05$) in all of the menopausal symptoms, contrasting to those of the control group where most of the improvements were insignificant. In addition, based on patient subjective self-evaluation of improvements, patents in the treatment groups reported a 74.3% overall effectiveness rate, contrasting to a 28.6% improvement of patients in the control group.

TABLE 6

Improvement of Menopausal Symptoms after Treatment of GLSs

| Group | | Fatigue (%) | Anorexia (%) | Palpitation (%) | forgetfulness (%) | irritation (%) | Depression (%) | impotence (%) |
|---|---|---|---|---|---|---|---|---|
| Treatment (n = 80) | Week 1 | 46 (57.5%) | 38 (47.5%) | 26 (32.5%) | 40 (50%) | 22 (27.5%) | 48 (60%) | 56 (70%) |
| | Week 2 | 56 (70%) | 50 (62.5%) | 30 (37.5%) | 42 (52.5%) | 30 (37.5%) | 56 (70%) | 56 (70%) |
| | Week 3* | 70 (85%) | 56 (70%) | 30 (37.5%) | 42 (52.5%) | 30 (37.5%) | 66 (82.5%) | 64 (80%) |
| Control (n = 58) | Week 1 | 15 (25%) | 11 (20%) | 3 (5%) | 7 (12.5%) | 6 (10%) | 11 (20%) | 14 (25%) |
| | Week 2 | 20 (35%) | 13 (22.5%) | 4 (7.5%) | 11 (20%) | 9 (15%) | 13 (22.5%) | 17 (30%) |
| | Week 3 | 22 (37.5%) | 16 (27.5%) | 4 (7.5%) | 16 (27.5%)) | 9 (15%) | 13 (22.5%) | 20 (35%) |

*$p < 0.05$

As shown in Table 7, 3 weeks of treatment with GLSs capsules significantly increased the blood levels of testosterone and SOD ($p<0.05$), contrasting to the baseline values of the treatment group as well as the values of the control group after receiving 3 weeks of placebo. The 3 weeks of treatment with GLSs capsules also significantly reduced the blood level of MDA ($p<0.05$) while no improvement was observed in the control group.

TABLE 7

Effects of GLSs on Blood Levels of Testosterone, SOD and MDA in Patients with Menopausal Symptoms

| Group | | Testosterone (ng/dL) | SOD ($\mu$/g · Hb) | MDA ($\mu$mol/L) |
|---|---|---|---|---|
| Treatment | baseline | 131.5 ± 19.12 | 1068.3 ± 121.4 | 7.6 ± 0.8 |
| (n = 68) | after treatment | 253.72 ± 21.45* | 1178.1 ± 132.6* | 5.8 ± 0.6* |
| Control | baseline | 143.56 ± 20.31 | 1023.3 ± 101.6 | 7.1 ± 0.5 |
| (n = 25) | after treatment | 150.44 ± 17.46 | 1048.3 ± 112.4 | 7.3 ± 0.7 |

*$p < 0.05$

As shown in Table 8, after 3 weeks of treatment with GLSs capsules, patients with menopausal symptoms in the treatment group showed statistically significant improvement in depression, as evident by the reduction in both Zung's and SRS scores. There was no significant improvement observed in the menopausal patients in the control group.

TABLE 8

Effects of on the Zung's score and SRS score

| Group | | baseline | Week 1 | Week 2 | Week 3 |
|---|---|---|---|---|---|
| Treatment | Zung's score | 54.36 ± 6.19 | 47.23 ± 6.93 | 42.71 ± 7.12 | 38.25 ± 6.56* |
| | SRS score | 21.26 ± 3.43 | 19.65 ± 3.14 | 17.96 ± 1.53 | 15.45 ± 3.42* |
| Control | Zung's score | 53.12 ± 7.31 | 52.81 ± 7.15 | 50.32 ± 7.63 | 48.41 ± 6.75 |
| | SRS score | 22.12 ± 3.84 | 21.56 ± 6.23 | 21.13 ± 5.16 | 20.45 ± 4.33 |

*$p < 0.05$

There were no remarkable adverse reactions reported by the patients receiving 3 weeks of GLSs capsules. Two patients reported transient constipation which disappeared after prolonged GLSs treatment. There were no water or salt retention, urination difficulty, hepatic dysfunction or renal dysfunction.

3. Discussions

Although modem medicines have greatly advanced in the understanding of geriatric diseases in recent years, it was not until 1960s that people realized the hormonal changes and accompanying diseases occurred during male aging process. The so-called "male menopause" is now accepted by the medical field. Some symptoms associated with the male menopause are similar to those in the women. However, the correlation between the hormonal changes (e.g., reduced sex hormone production, reduced activity of Leydig cells, sexual dysfunction) and the neuronal functions (e.g., reduced responses of hypothalamus and pituitary gland) for male menopause are not yet established.

Because of the large variations among individuals, the blood level of testosterone can not be the sole indicator for diagnosis of male menopause. The mental status also has an impact on man's sexual drive, rendering clinical observation difficult. Thus we design the study of GLSs on male menopausal syndromes using objective indices (e.g., blood levels of testosterone, SOD and MDA) and mental evaluation (e.g., SRS and Zung's scores) to observe overall treatment effects.

The free radical theory of aging supports the relationship between free radical damage and the aging process. Free radicals have a close relationship with the onset and progress of geriatric male menopausal symptoms. Under normal physiological conditions, SOD can effectively remove the superoxide free radicals, prevent free radical chain reactions, and maintain body's balance between production and removal of free radicals. If, for any reason, free radicals are overproduced or body's removal ability is reduced, the homeostasis of the body will be destroyed, this may lead to deregulation of the endocrine system which speeds up the aging process.

The observation that testosterone production decreased with the increases in age was first reported in 1948. About 20% of men 60 years of age or above have blood testosterone levels below the normal value. It is found that the blood testosterone level can influence the neural functions in men affecting behaviors such as sexual arousal, attacks, feeling and cognition. Effects of reduced testosterone production on male mental status are under investigation, although there has been evidence which supports the association of depression with low blood testosterone level.

In the present study, the activity of SOD was measured as an indicator for the body's ability to remove free radicals and the level of MDA as an indicator for the presence of free radical damage. It was found that treatment with GLSs markedly increased the turnover of free radicals as evident by increased SOD activity and reduced MDA levels. Results of SRS and Zung's scores suggested that low testosterone levels led to depression, which in turn was associated with different degrees of sexual dysfunction (e.g., impotence). Treatment with GLSs not only effectively increased the blood levels of testosterone but also markedly increased the body's ability to remove free radicals.

In comparison, the patients in the control group showed improvement due to the placebo effect as placebo might provide a psychological treatment effect. However, the overall improvement rate of 28.6% in the control group was statistically significant lower than the 74.3% overall improvement rate reported by the patients treated with GLSs.

Currently, geriatric male menopausal symptoms are frequently treated with testosterone supplement therapy. However, the risks associated with the hormonal supplement affect the cardiovascular system and the prostate. Metabolites of the male hormone may induce insulin resistance and increase the endothelin level (causing blood vessel constriction), thus adversely affecting the cardiovascular system and increasing the incidence of cardiovascular diseases. As a result, cardiovascular insufficiency is a contraindication for the testosterone supplement treatment. In terms of treatment risks on prostate, there is no direct evidence that testosterone supplement treatment causes prostate cancers. However, clinical data indicate that testosterone can increase the tumor growth in patients with prostate cancers.

The uses of *ganoderma*, particularly the spores, have become the targets of many studies in recent years since the development of cultivation method. However, most of the studies were conducted using intact spores (non-wall broken). In contrast, the GLSs capsules used in this clinical trial were produced using the germination-activation technique described in U.S. Pat. No. 6,316,002 B1. These sporoderm-broken spores exhibit more potent anti-oxidative and endocrine regulating activities, because this technique allows all the active genetic materials of the spores to be available for producing the therapeutic effects.

4. Conclusion

GLSs are a better treatment choice for the geriatric male menopausal symptoms because they are scavengers of free radicals. In addition, GLSs promote testosterone production, alleviate depression, and delay the aging process without the adverse side effects of the hormonal supplement therapy.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for reducing risk of age-related disorders in a human comprising:

orally administering to said human an effective amount of sporoderm-broken germination activated *Ganoderma lucidum* spores (GLSs);

whereby said sporoderm-broken GLSs are prepared by soaking *ganoderma* spores in a solution which is selected from the group consisting of water, saline, and a nutritional solution to cause the spores to germinate;

placing said germination-treated *ganoderma* spores in a culture box at a relative humidity of 65–98% and temperature of 18–48 degree C. to cause the germinated *ganoderma* spores to activate; and breaking sporoderm of said germination activated *ganoderma* spores to produce said sporoderm-broken GLSs.

2. The method according to claim 1, wherein said sporoderm-broken GLSs display antioxidant activity.

3. The method according to claim 2, wherein said effective amount of said sporoderm-broken GLSs is in the amount of 0.5 to 10 g per day.

4. The method according to claim 3, wherein said sporoderm-broken GLSs are given to said human in the amount of 1 to 5 g per day.

5. The method according to claim 2, wherein said sporoderm-broken GLSs increase a reduced form glutathione (GSH) and a superoxide dismutase (SOD) activity in said human.

6. The method according to claim 1, wherein said human is a male.

7. The method according to claim 1, wherein said patient is an elderly human.

8. The method according to claim 6, wherein said sporoderm-broken GLSs increase testosterone in blood of said human.

9. The method according to claim 6, wherein said sporoderm-broken GLSs increase superoxide dismutase (SOD) in blood of said human.

10. The method according to claim 1, wherein said sporoderm-broken GLSs decrease malondialdehyde (MDA) in blood of said human.

11. The method according to claim 1, wherein said sporoderm-broken GLSs improve depression of said human.

12. The method according to claim 6, wherein said age-related disorders are at least one selected from the group consisting of fatigue, anorexia, palpitation, forgetfulness, irritation, and impotence.

* * * * *